US007256025B2

(12) United States Patent
Goto

(10) Patent No.: US 7,256,025 B2
(45) Date of Patent: Aug. 14, 2007

(54) GENE IMPROVING TEMPERATURE-TOLERANCE OF ACETIC ACID BACTERIUM, ACETIC ACID BACTERIUM BRED USING THE GENE AND PROCESS FOR PRODUCING VINEGAR USING THE ACETIC ACID BACTERIUM

(75) Inventor: Hidetsugu Goto, Hokkaidou (JP)

(73) Assignee: Mitsukan Group Corporation, Handa-shi (JP)

( * ) Notice: Subject to any disclaimer, the term of this patent is extended or adjusted under 35 U.S.C. 154(b) by 120 days.

(21) Appl. No.: 10/538,481

(22) PCT Filed: Dec. 4, 2003

(86) PCT No.: PCT/JP03/15542

§ 371 (c)(1),
(2), (4) Date: Jun. 7, 2005

(87) PCT Pub. No.: WO2004/053122

PCT Pub. Date: Jun. 24, 2004

(65) Prior Publication Data

US 2006/0286652 A1    Dec. 21, 2006

(30) Foreign Application Priority Data

Dec. 9, 2002   (JP) ............................. 2002-356844

(51) Int. Cl.
*C12N 9/10* (2006.01)
*C12N 1/20* (2006.01)
*C12N 15/74* (2006.01)
*C12P 7/54* (2006.01)
*C12P 21/06* (2006.01)

(52) U.S. Cl. .................. 435/140; 435/69.1; 435/252.3; 435/471; 435/320.1; 435/193; 536/23.2

(58) Field of Classification Search ................ 435/200, 435/220, 69.1, 235.1; 536/23.1, 23.2
See application file for complete search history.

(56) References Cited

FOREIGN PATENT DOCUMENTS

| JP | 54-46899 | 4/1979 |
|---|---|---|
| JP | 60-9488 | 1/1985 |
| JP | 2002-95493 | 4/2002 |
| JP | 2005-110597 | 4/2005 |

OTHER PUBLICATIONS

Leipelt et al., Glucosylceramide synthases, a gene family responsible for the biosynthesis of glucosphingolipids in animals, plants and fungai JBC., 2001, vol. 276(36): 33621-33629..*
Jorasch et al., Novel processive and nonprocessive glycosyltransferases from *Staphylococcus aureus* and *Arabidopsis thaliana* synthesize glycoglycerolipids, glycophospholipids, glycosphingolipids and glycosterols. Eur. J. Bioche., 2000, vol. 267: 3770-3783.*
Saito et al., Molecular cloning of chinese hamster ceramide glucosyltransferase and its enhanced expression in peroxisome-derived mutant Z65 cells. Arch. Biochem and Biophysics., 2002, vol. 403: 171-178.*
Shouji Ohmori: "Isolation and Identification of Acetic Acid Bacreria for Submerged Acetic Acid Fermentational High Temperature", Agric. Biol. Chem., vol. 44, No. 12, pp. 2901-2906, 1980.
Thomas J. White: "The polymerase chain reaction", Trends in Genetics, vol. 5, No. 6, pp. 185-189, 1989.
Masahiro Fukaya: "Cloning of the Membrane-Bound Aldehyde Dehydrogenase Gene of Acetobacter polyoxogenes and Improvement of Acetic Acid Production by Use pf the Cloned Gene", Applied and Environmental Microbiology, vol. 55, No. 1, pp. 171-176, Jan. 1989.
Hajime Okumura: "Cloning the β-Isopropylmalate Dehydrogenase Gene from Acetobacter aceti and Its Use for Construction of a New Host-vector System for Acetobacter", Agric. Biol. Chem., vol. 52, No. 12, pp. 3125-3129, 1988.
Masahiro Fukaya: "Improved Transformation Method for Acetobacter with Plasmid DNA", Agric. Biol. Chem., vol. 49, No. 7, pp. 2091-2097, 1985.
Kenji Tayama: "Transformation of Acetobacter polyoxogenes with Plasmid DNA by Electroporation", Biosci. Biotech. Biochem., vol. 58, No. 5, pp. 974-975, 1994.
M. Fujiwara: "17 Construction of shuttle vectors and a genetic transformation system for cellulose-producing bacteria: "*Acetobacter xylinum*, Cellulose, pp. 153-158, 1989.
Hiroshi Takemura: "Induction by Ethanol of Alcohol Dehydrogenase Activity in Acetobacter pasteurianus", Journal of Bacteriology, vol. 175, No. 21, pp. 6857-6866, Nov. 1993.
Ching-Hui Yeh et al., "Expression of a gene encoding a 16,9-kDa Heat-shock protein, Oshsp 16.9, *Escherichia coli* enhances thermotolerance", Proceedings of the National Academy of Sciences of USA, vol. 94, No. 20, pp. 10967-10972 Sep. 30, 1997.
Kaneko T. et al., "Sequence analysis of the genome of the unicellular cyanobacterium synechocystis sp. strain PCC6803.II Sequence determination of the entire genome and assignment of potential protein-coding regions", DNA Research: an International Journal for Rapid Publication of Reports on Genes and Genomes, vol. 3, No. 3, pp. 109-136 Jun. 30, 1996.
O. Adachi, et al., "New developments in oxidative fermentation", Applied Microbiology and Biotechnology, vol. 60, No. 6, pp. 643-649 2003.

* cited by examiner

*Primary Examiner*—Rebecca E. Prouty
*Assistant Examiner*—Ganapathirama Raghu
(74) *Attorney, Agent, or Firm*—Oblon, Spivak, McClelland, Maier & Neustadt, P.C.

(57) ABSTRACT

The present invention is intended to provide a novel gene originating in an acetic acid bacterium, which participates in temperature tolerance; a method of improving the temperature tolerance of a microorganism, in particular, an acetic acid bacterium using the above gene; and a method of efficiently producing vinegar having a higher acetic acid concentration with the use of an acetic acid bacterium whose temperature tolerance has been improved.

17 Claims, 10 Drawing Sheets

Fig. 2
FERMENTATION PROCESS OF ORIGINAL STRAIN
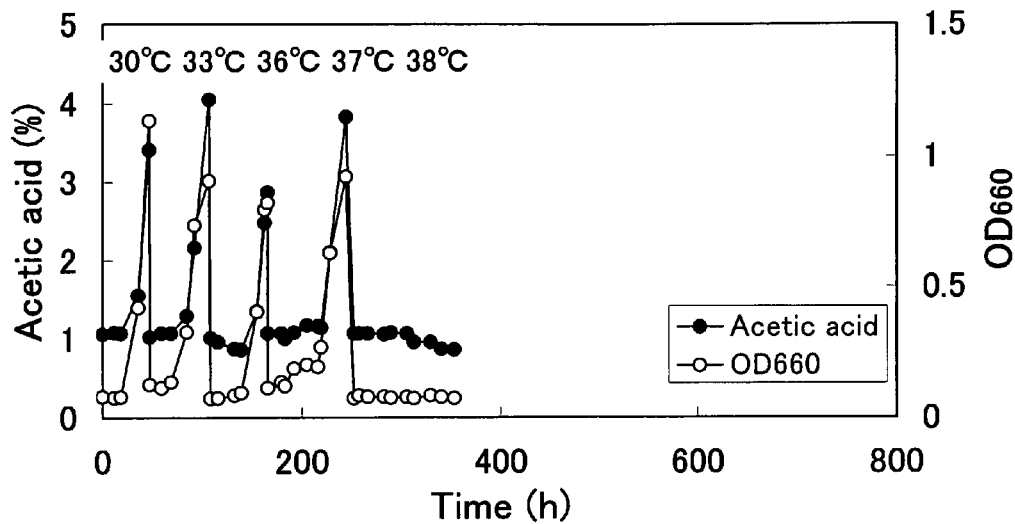
FERMENTATION PROCESS OF TRANSFORMANT
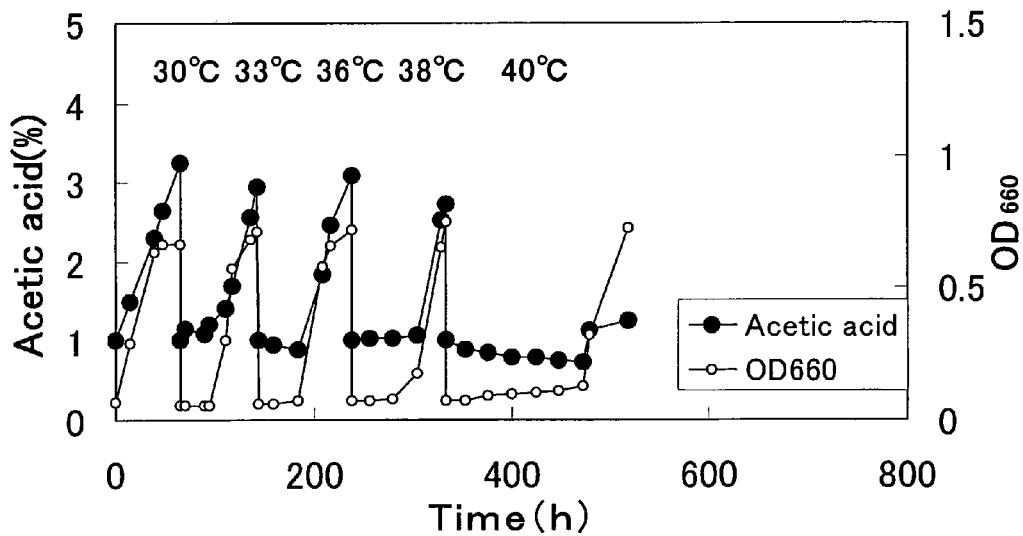

Fig. 3
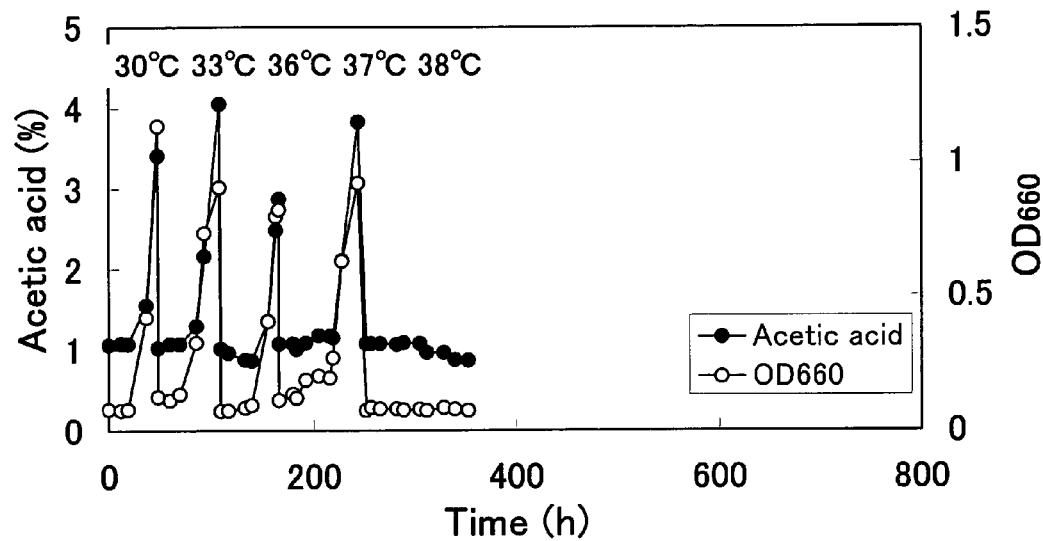
FERMENTATION PROCESS OF ORIGINAL STRAIN
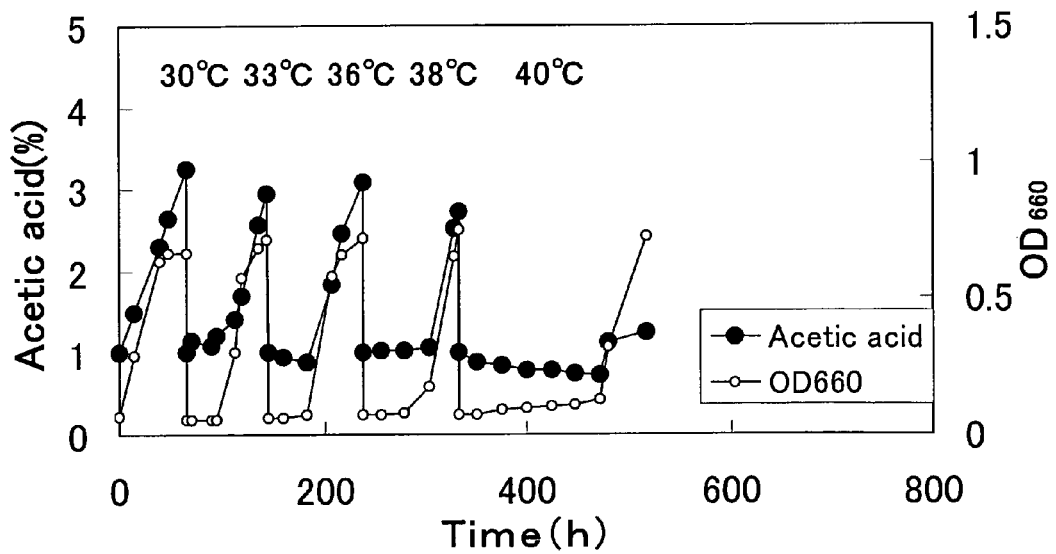
FERMENTATION PROCESS OF TRANSFORMANT

Fig. 4

| | | |
|---|---|---|
| MetSerValPheAsnAlaLeuValSerPro | AlaGlyLeuAlaAlaThrValAlaValAla | 20 |
| GlyCysMetGlnAlaAlaLeuGlyThrPhe | LeuValSerArgPheArgTrpGlnGluLys | 40 |
| ArgMetAspArgAlaValProMetProPro | ValSerValLeuLysProLeuHisGlyAsp | 60 |
| GluProLeuLeuGluGluAlaLeuGluSer | PheCysThrGlnAspTyrProGlnMetGln | 80 |
| IleValPheGlyValGlnAlaGluAspAsp | AlaAlaIleProIleValGlnArgLeuMet | 100 |
| GluArgHisProAspValGlnMetGluLeu | ValIleAspProThrPheHisGlyLeuAsn | 120 |
| ArgLysIleGlyAsnLeuIleAsnIleMet | ThrArgValLysHisAspValLeuValIle | 140 |
| SerAspSerAspIleHisValAlaProAsp | TyrLeuArgHisValValGlyAlaMetVal | 160 |
| ProAspAsnValGlyLeuValThrThrLeu | TyrAlaGlyLeuProAlaSerSerThrLeu | 180 |
| ProArgLeuLeuAlaAlaCysGlnIleAsn | HisAsnPheLeuProGlyValMetLeuSer | 200 |
| LeuTyrLeuGlyArgGlnAspCysLeuGly | AlaThrMetAlaLeuArgArgSerMetLeu | 220 |
| AspGluIleGlyGlyLeuGluAlaLeuVal | ProHisValAlaAspAspAlaIleLeuGly | 240 |
| ArgTyrValArgAspArgGlyLysAspIle | AlaIleAlaAlaCysMetThrTrpThrThr | 260 |
| ValGlyGluThrSerMetArgGluValLeu | AlaHisGluLeuArgTrpGlyArgThrVal | 280 |
| LysThrLeuGluProAlaGlyTyrAlaAla | SerAlaIleGlnLeuProLeuPheTrpAla | 300 |
| SerValAlaValLeuAlaAlaProHisAla | ThrTrpThrTrpSerPhePheLeuGlyAla | 320 |
| TrpGlyTrpArgAlaValCysSerPheIle | LeuAspArgThrLeuAlaGlnArgSerLeu | 340 |
| ValLeuProSerLeuLeuLeuProLeuArg | AspTrpIleSerAlaAlaValMetValGly | 360 |
| SerValThrGlyThrArgValAlaTrpArg | GlyGlnThrMetHisValThrProHisSer | 380 |
| ValMetThrProArgSerGlnProAlaSer | ProGlyAsp | 393 |

Fig. 5

5'-GAAGAGTGATATTACACTTCCCTGACGCCG-3'

Fig. 6

5'-CCCGTTCTTATTAACGACAGGGTTGG-3'

Fig. 7

```
gaagagtgat attacacttc cctgacgccg ttttctaatt tgctccatac gcgggacctt    60
gccggaaaga taatgtctgt tttcaacgct cttgtttcac ccgccggact ggccgcgacc   120
gttgcggtcg ccgggtgcat gcaggcagcg cttggcactt ttctggtctc gcgtttccgg   180
tggcaggaaa aacgcatgga ccgggcggtg cccatgcctc cggtttccgt gctcaagccc   240
ctccacggcg atgaaccgct gctggaggaa gcgcttgaaa gcttctgcac gcaggattac   300
ccgcagatgc agatcgtctt tggcgtacag gccgaagacg atgcggcgat cccgatcgta   360
caacggttga tggaacgcca cccggatgtg cagatggaac tggtgattga ccccaccttc   420
cacgggctca accgcaagat cggcaacctg atcaacatca tgacgcgcgt gaagcatgat   480
gtcctggtca tttccgattc ggatatccac gttgccccccg attacctgcg gcatgtggtg   540
ggcgccatgg tgcccgacaa tgtcggcctg gtcacgacgc tgtacgcggg gctgcccgcg   600
tcatccacgc tgccgcgcct gctggccgca tgccagatca accataactt cctgcccggc   660
gtgatgctgt cactctacct cgggcggcag gactgccttg gggcgacaat ggcgctgcgg   720
cgttccatgc tggacgaaat cggcggggctg gaagccctcg tgccgcatgt ggccgatgat   780
gcgatactgg gccgttacgt gcgtgaccgt ggcaaggata tcgccattgc cgcgtgcatg   840
acctggacca ccgtgggcga gacctcgatg cgtgaggtgc tggcgcatga actgcgctgg   900
ggccggaccg tcaagacgct ggagcctgcg ggttatgccg catccgccat ccagctgccc   960
ctgttctggg ccagcgtcgc cgtgcttgcc gcgccgcatg cgacctggac atggtccttc  1020
tttcttggtg catggggatg gcgggccgtg tgttccttca tcctggaccg tacgctggcg  1080
caacgtagtc tggtgctgcc gtcactgctt ctgccactgc gcgactggat ctcggccgcc  1140
gtcatggtgg gcagtgtcac tggcacgcgg gttgcatggc gtgggcagac aatgcatgtc  1200
acgccccatt cggtcatgac accacgatcg caaccggctt cccccggtga ctgacccgcc  1260
gtcagcaggc tgaactgctt gagaattcca accctgtcgt taataagaac ggg         1313
```

Fig. 9

```
catggggcgt cacccccagc ggccagcttg gctacctgat ggacagggcg ggccttctgc    60
aagccctcgg ccactgccat ctgccgggat atgaggccaa atacgaaccg aaggaaaagc   120
gcaccttctg ctaccccacc cagaacgcca gcggctgggc tgtgcagcca tgatcgccaa   180
cccctccctc ttcctgagca attcggaaga gcgatttccg ccgactgaac acgtcgaaaa   240
tggcagtttt ccaccgaaaa aaggaaagga ccataggaaa ggattaatat cttattttta   300
tctaggggtt tgccgatccg cgattttcgc tgggaaaccg ccaaaaatgg cttgccatta   360
ggtcgcacca catgcgacca taaagtcgca cagtgtgcga cctattcggc ccatatacag   420
aggttcccca catgcggaat gtcacccgtc tcaagacccg caaagaccgg ctccgcgagg   480
accaagccga cctgttgaag caagcccttc tgcccttcgc agaggacgat ggaccgatgc   540
gggatgcggt cggacggctc tacgtccaga tcaagaacct caccacccca gaccccggaa   600
ccacggagcc gttcgtcatg atccgtcccg cccagaatcg cgccgtcacc ctctggctgc   660
tgaagaacag taagcggccc atgaaggccg tggacgtatg gacgctgctg ttcgaccacc   720
tgtttcccca taccggccag atcatgctga cccgtgagga aatcgcggaa aaagtcggta   780
tccgggtcaa cgaagttaca gccgtcatga acgagctggt gagcttcggc gcgattttct   840
ccgagcgcga gaaggtggcc ggaatgcgcg ggccgggcct cgcccgctac tacatgaacc   900
ggcatgtggc cgaggtcggc agccgcgcca cgcaggaaga acttgcccta atcccacgcc   960
ccggcgccaa gctggcagtc gtgcagggtg gcaaggctta acccatgaag gtttcggaac  1020
tggacgtgtt cgacagcgcc aaggcggcac aagacccgtt ggtgcgggaa gaactgctgc  1080
aagcagcgca ggcggacggc cacggccccg ccctcgctca tgcccgttcc gtcatagcca  1140
aggcgcgggc cgggcaggac gccaaggctt aacggccccg ccctctcccg cctcgatccc  1200
ggcgggcctg tagcatctcc tgatgctcct tggcgttttt ggcccgctgc tcggcccgct  1260
ctttctcggc cgctgcggct cttaggcgct cttcggccag ccgcatccgc tcgtccatct  1320
gacgtttccg atctgcctcg gcatccttgg cggctcctgc cttcagccct ttgctgaaag  1380
ccatccactt attggcggtt ttctcggctt tctgctgtat cggcggggtc agccggtcaa  1440
atgcctgggc caccctctcg aagccctcac gcatggcgtt gacggcctgc gccagtttag  1500
ccagggcgaa atctatcacc tcggcccgct gggcgttctc ggcccggata cgccggttgt  1560
ggttgccggt cggggtctgg tgcccttcc gttccagagc caccacattc ggccccatgt  1620
gccgctctgg aacgcggtct agccctgct ccgcattgct ccggtgatct atccgggcct  1680
cttgcccagc ccgctctagc gcggcattgg caaggcccgc ccatagctgc cggatttcct  1740
tcacctcgtc ggcggccttc cccagtccca tgccctgccg cttcttgtcg acagttcga   1800
tggttgattt gtctccaaag gacagcttgc catcggcccc ccgctccacc gtgcgggtgg  1860
tggtcatgat gtgcgcgtga tgattccggt cgtcgccctc gtcacccgga agatgcacgg  1920
```

Fig. 10

```
ccacgtccac ggccaccccg taccgctgga ccaactcacg cgcgaaactg tccgccagtt  1980
cggcccgctg ctcgctggtg agttcatgag ggagggccac aacccattcc ctcccggtgc  2040
gggcgtcctt gcgtttctct gatcgctccg cgtcattcca caattccgaa cggtcagcgg  2100
tgccaccccc cggaatgaaa attgccttat gggcaacgct attctgcctg gggctgtatt  2160
tgtgttcgtg cccgtcaacc tcgttggtca aatcctcgcc agcacgatac gcagccgcag  2220
ccacaacgga acgccctgcg ctccggctga tcggtttcgt ttctgcgcga tagattgcca  2280
cggatcgagc gcctaccttt tggagttaaa cggggggttc aggggggcga agccaccatg  2340
acgcaggact tgcacttgtg caagtcgtaa ctgcgccctt aatacctgac ggcatcaagg  2400
gatatgtggt attcgtttga aacggaacgg ctccacggtg aggatgatat gagcgatatt  2460
gcgaaagaga ttgagaacgc caaaggatc atagctgaac agaaaaagcg catcaaagat  2520
gcccagaagg aagcagctaa agcggaatca aagttgaggg accgtcagaa ctacatcttg  2580
ggcggcgcac tggtaaaact tgccgaaaca gatgaacggg ccgtccgcac tattgaaaca  2640
cttttgaagc tggtggatcg tccatcagac cggaaggcgt ttgaggtgtt ttcccgtctc  2700
ccatccctct ccctgcccac gcagccagca ccggacaccg gccatgagtg aggcactgga  2760
agaagatccg tttgaactgt tcaaaagggt cgaaaaaagc ctgtccacgg ccaccgccag  2820
catggagcgg ctggccgccg aacaagatgc caggtgcaag accatttcag acgccgccgg  2880
aaaagcctct aaattggccg aggaagccgg tgacaccttc acagcatcca agaggcgtct  2940
gatgatctgg acggccctct gcgcggctct gctggtctgt ggcgggtggt tggcgggtta  3000
ttggctggga caccgtgacg gttgggcctc tgcacggcc cacgacgtct aagaaaccat  3060
tattatcatg acattaacct ataaaaatag gcgtatcacg aggccctttc gtctcgcgcg  3120
tttcggtgat gacggtgaaa acctctgaca catgcagctc ccggagacgg tcacagcttg  3180
tctgtaagcg gatgccggga gcagacaagc ccgtcagggc gcgtcagcgg gtgttggcgg  3240
gtgtcggggc tggcttaact atgcggcatc agagcagatt gtactgagag tgcaccatat  3300
gcggtgtgaa ataccgcaca gatgcgtaag gagaaaatac cgcatcaggc gccattcgcc  3360
attcaggctg cgcaactgtt gggaagggcg atcggtgcgg gcctcttcgc tattacgcca  3420
gctggcgaaa gggggatgtg ctgcaaggcg attaagttgg gtaacgccag ggttttccca  3480
gtcacgacgt tgtaaaacga cggccagtgc caagcttgca tgcctgcagg tcgactctag  3540
aggatccccg ggtaccgagc tcgaattcgt aatcatggtc atagctgttt cctgtgtgaa  3600
attgttatcc gctcacaatt ccacacaaca tacgagccgg aagcataaag tgtaaagcct  3660
ggggtgccta atgagtgagc taactcacat taattgcgtt gcgctcactg cccgctttcc  3720
agtcgggaaa cctgtcgtgc cagctgcatt aatgaatcgg ccaacgcgcg gggagaggcg  3780
gtttgcgtat tgggcgctct tccgcttcct cgctcactga ctcgctgcgc tcggtcgttc  3840
ggctgcggcg agcggtatca gctcactcaa aggcggtaat acggttatcc acagaatcag  3900
gggataacgc aggaaagaac atgtgagcaa aaggccagca aaaggccagg aaccgtaaaa  3960
aggccgcgtt gctggcgttt ttccataggc tccgcccccc tgacgagcat cacaaaaatc  4020
gacgctcaag tcagaggtgg cgaaacccga caggactata agataccagg cgtttcccc   4080
```

Fig. 11

```
ctggaagctc cctcgtgcgc tctcctgttc cgaccctgcc gcttaccgga tacctgtccg   4140
cctttctccc ttcgggaagc gtggcgcttt ctcaatgctc acgctgtagg tatctcagtt   4200
cggtgtaggt cgttcgctcc aagctgggct gtgtgcacga acccccgtt cagcccgacc    4260
gctgcgcctt atccggtaac tatcgtcttg agtccaaccc ggtaagacac gacttatcgc   4320
cactggcagc agccactggt aacaggatta gcagagcgag gtatgtaggc ggtgctacag   4380
agttcttgaa gtggtggcct aactacggct acactagaag gacagtattt ggtatctgcg   4440
ctctgctgaa gccagttacc ttcggaaaaa gagttggtag ctcttgatcc ggcaaacaaa   4500
ccaccgctgg tagcggtggt ttttttgttt gcaagcagca gattacgcgc agaaaaaaag   4560
gatctcaaga agatcctttg atcttttcta cggggtctga cgctcagtgg aacgaaaact   4620
cacgttaagg gattttggtc atgagattat caaaaaggat cttcacctag atccttttaa   4680
attaaaaatg aagttttaaa tcaatctaaa gtatatatga gtaaacttgg tctgacagtt   4740
accaatgctt aatcagtgag gcacctatct cagcgatctg tctatttcgt tcatccatag   4800
ttgcctgact ccccgtcgtg tagataacta cgatacggga gggcttacca tctggcccca   4860
gtgctgcaat gataccgcga gacccacgct caccggctcc agatttatca gcaataaacc   4920
agccagccgg aagggccgag cgcagaagtg gtcctgcaac tttatccgcc tccatccagt   4980
ctattaattg ttgccgggaa gctagagtaa gtagttcgcc agttaatagt ttgcgcaacg   5040
ttgttgccat tgctacaggc atcgtggtgt cacgctcgtc gtttggtatg gcttcattca   5100
gctccggttc ccaacgatca aggcgagtta catgatcccc catgttgtgc aaaaaagcgg   5160
ttagctcctt cggtcctccg atcgttgtca gaagtaagtt ggccgcagtg ttatcactca   5220
tggttatggc agcactgcat aattctctta ctgtcatgcc atccgtaaga tgcttttctg   5280
tgactggtga gtactcaacc aagtcattct gagaatagtg tatgcggcga ccgagttgct   5340
cttgcccggc gtcaatacgg gataataccg cgccacatag cagaacttta aaagtgctca   5400
tcattggaaa acgttcttcg gggcgaaaac tctcaaggat cttaccgctg ttgagatcca   5460
ttcgatgtaa cccactcgtg cacccaactg atcttcagca tcttttactt tcaccagcgt   5520
ttctgggtga gcaaaaacag gaaggcaaaa tgccgcaaaa aagggaataa gggcgacacg   5580
gaaatgttga atactcatac tcttcctttt tcaatattat tgaagcattt atcagggtta   5640
ttgtctcatg agcggataca tatttgaatg tatttagaaa aataaacaaa taggggttcc   5700
gcgcacattt ccccgaaaag tgccacctga cgtc                               5734
```

Fig. 12 cgctgacgtc gtgggccgtg ccagaggccc

Fig. 13 ggccaagacg tctgcagcat ggggcgtcac

GENE IMPROVING TEMPERATURE-TOLERANCE OF ACETIC ACID BACTERIUM, ACETIC ACID BACTERIUM BRED USING THE GENE AND PROCESS FOR PRODUCING VINEGAR USING THE ACETIC ACID BACTERIUM

TECHNICAL FIELD TO WHICH THE INVENTION PERTAINS

The present invention relates to a gene that encodes a protein having a function of enhancing temperature tolerance derived from a microorganism, a microorganism in which the copy number of the gene is amplified, particularly an acetic acid bacterium which belongs to the genus *Acetobacter* or the genus *Gluconacetobacter*, and a method of efficiently producing vinegar containing acetic acid at a high concentration by using such a microorganism.

PRIOR ART

In industrial vinegar production, acetic acid fermentation by microorganisms is utilized. Such microorganisms have alcohol oxidation ability and are generally called acetic acid bacteria. Among acetic acid bacteria, particularly acetic acid bacteria which belong to the genus *Acetobacter* or the genus *Gluconacetobacter* are widely utilized for industrial acetic acid fermentation.

In acetic acid fermentation, ethanol in a medium is oxidized and converted to acetic acid by acetic acid bacteria, and as a result, acetic acid accumulates directly in the medium. At this time, a large amount of heat of fermentation is generated, and as a result, the temperature in the fermentation liquid increases when it is left alone as it is. An optimal fermentation temperature for acetic acid bacteria is generally around 30° C., therefore, it is necessary to cool the fermentation liquid in order not to increase the temperature thereof, which results in needing energy for cooling. Accordingly, it is required in acetic acid fermentation that growth ability and fermentation ability do not decrease even at a higher temperature, i.e. development of acetic acid bacteria having strong temperature tolerance is required. It has been attempted as one of the means that temperature-tolerant acetic acid bacteria are searched by screening acetic acid bacteria with temperature tolerance from nature (see, non-patent literature 1, for instance).

However, there are few findings on temperature-tolerance genes of acetic acid bacteria, and it was desired to obtain a novel temperature-tolerance gene that encodes a protein having a function capable of improving the temperature tolerance of acetic acid bacteria on a practical level and to breed acetic acid bacteria having stronger temperature tolerance with the use of the obtained temperature-tolerance gene.

Patent literature 1
  Japanese Laid-Open Patent Application No. 60-9488

Patent literature 2
  Japanese Patent Application No. 2003-350265

Non-patent literature 1
  Agricultural and Biological Chemistry, vol. 44, p. 2901-2906, 1980

Non-patent literature 2
  Trends in Genetics, vol. 5, p. 185-189, 1989

Non-patent literature 3
  Applied and Environmental Microbiology, vol. 55, p. 171-176, 1989

Non-patent literature 4
  Agricultural and Biological Chemistry, vol. 52, p. 3125-3129, 1988

Non-patent literature 5
  Agricultural and Biological Chemistry, vol. 49, p. 2091-2097, 1985

Non-patent literature 6
  Bioscience, Biotechnology and Biochemistry, vol. 58, p. 974-975, 1994

Non-patent literature 7
  Cellulose, p. 153-158, 1989

Non-patent literature 8
  Journal of Bacteriology, vol. 175, 6857-6866, 1993

Problem to be Solved by the Invention

As mentioned above, no example that has elucidated temperature tolerance of acetic acid bacteria on a genetic level and has succeeded in the development of practically usable acetic acid bacteria having high temperature tolerance has been reported heretofore. However, development of acetic acid bacteria superior in temperature tolerance would allow the performance of acetic acid fermentation at a higher temperature than conventionally and reduction of the cost of cooling. Therefore, the present inventor attempted again to elucidate the improvement of temperature tolerance of acetic acid bacteria on a genetic level.

As a result of consideration from various aspects, and from the view point that it was important to obtain a novel temperature-tolerance gene that encodes a protein having a function capable of improving temperature tolerance on a practical level and to breed acetic acid bacteria having stronger temperature tolerance with the use of the obtained temperature-tolerance gene, the present inventor has newly set novel technical tasks to provide a novel gene for improving temperature tolerance, which participates in temperature tolerance and is derived from a microorganism belonging to acetic acid bacteria, and to provide a method of improving temperature tolerance of a microorganism by using the gene, particularly a method of improving temperature tolerance of a microorganism belonging to acetic acid bacteria, further a method of efficiently producing vinegar by using the acetic acid bacteria whose temperature tolerance was improved.

MEANS FOR SOLVING PROBLEMS

The present inventor hypothesized that a specific gene participating in temperature tolerance that does not exist in other microorganisms should exist in acetic acid bacteria capable of growing and fermenting even under a high temperature, and obtained a novel concept that the use of such a gene would allow the improvement of temperature tolerance of a microorganism more than before and the development of an efficient production method.

As for a method of obtaining a temperature-tolerance gene in the conventional methods, a method of screening a temperature-insensitive mutant was popular.

However, thinking that it was difficult to find a temperature-tolerance gene, which was industrially useful, by such a method, the present inventor has investigated another acquisition method. As a result, the inventor developed a method of obtaining a gene enabling acetic acid bacteria, which can generally grow only at around 37° C. on an agar medium, to grow under a temperature of 38° C. by constructing a chromosomal DNA library of acetic acid bacteria, transforming acetic acid bacteria with this chromosomal DNA library, and screening the target gene.

According to the use of this method, the present inventor has succeeded for the first time in cloning DNA coding for a novel temperature-tolerance gene that has a function of enhancing temperature tolerance on a practical level from acetic acid bacteria belonging to the genus *Gluconacetobacter* practically used in producing vinegar.

The obtained temperature-tolerance gene showed homology with a group of proteins referred to as ceramide glucosyltransferase found in leguminous bacteria and the like, and it was presumed as a gene that encodes ceramide glucosyltransferase of acetic acid bacteria as a result of homology search on DDBJ/EMBL/Genbank.

However, the obtained ceramide glucosyltransferase gene of acetic acid bacteria had an extremely low homology with known ceramide glucosyltransferase genes found in other microorganisms such as leguminous bacteria. Therefore, it was found that, though it was similar to other ceramide glucosyltransferase genes to some extent, the obtained gene was a novel gene encoding a novel protein (it is sometimes referred to as protein GCS) specific to acetic acid bacteria.

In addition, the present inventor found that, in the case where the transformant was cultured with aeration in the presence of ethanol, the temperature tolerance was remarkably improved, the final acetic acid concentration can be remarkably improved, etc., and further have succeeded in determination of the amino acid sequence of the protein and the nucleotide sequence of the DNA of the gene encoding the protein, thus the present invention has been completed.

BRIEF DESCRIPTION OF THE DRAWINGS

FIG. 2 This is a figure showing the time course in acetic acid fermentation by the transformant in which the copy number of GCS gene was amplified.

FIG. 3 This is a figure showing the time course in acetic acid fermentation by the transformant in which the copy number of GCS gene was amplified.

FIG. 4 This is a figure showing the amino acid sequence (SEQ. ID No. 2) of the protein encoded by GCS gene.

FIG. 5 This is a figure showing primer 1.

FIG. 6 This is a figure showing primer 2.

FIG. 7 This is a figure showing the nucleotide sequence (SEQ. ID No. 1) of the present temperature-tolerance gene.

FIG. 9 This is a figure showing the nucleotide sequence (SEQ. ID No. 5) of pGI18.

FIG. 10 This is a figure showing the nucleotide sequence (SEQ. ID No. 5) of pGI18 continued from FIG. 9.

FIG. 11 This is a figure showing the nucleotide sequence (SEQ. ID No. 5) of pGI18 continued from FIG. 10.

FIG. 12 This is a figure showing primer A.

FIG. 13 This is a figure showing primer B.

DISCLOSURE OF THE INVENTION

Figure 1:
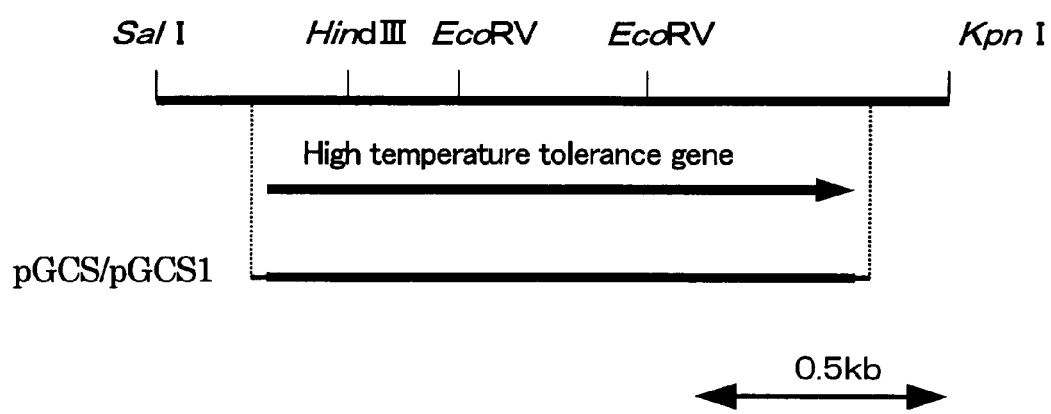
FIG. 1 This is a schematic view showing a restriction enzyme map of a gene fragment (pG1) derived from *Gluconacetobacter entanii* cloned by using restriction enzymes SalI and KpnI, the location of GCS gene and the insert into pGCS and pGCS1.

That is, the present invention provides the following (1) to (10) as examples of the embodiment.

(1) A protein GCS shown in the following (A) or (B):
(A) a protein having an amino acid sequence shown in SEQ. ID No. 2 in the sequence listing,
(B) a protein consisting of an amino acid sequence comprising substitution, deletion, insertion, addition, or inversion of one or several amino acids in an amino acid sequence shown in SEQ. ID No. 2 in the sequence listing and having a function of enhancing temperature tolerance.

(2) A DNA of a novel gene encoding a protein shown in the following (A) or (B):
(A) a protein having an amino acid sequence shown in SEQ. ID No. 2 in the sequence listing,
(B) a protein consisting of an amino acid sequence comprising substitution, deletion, insertion, addition, or inversion of one or several amino acids in an amino acid sequence shown in SEQ. ID No. 2 in the sequence listing and having a function of enhancing temperature tolerance.

(3) The DNA of a gene described in the above-mentioned (2), which is a DNA shown in the following (a) or (b):
(a) a DNA that comprises a nucleotide sequence consisting of nucleotides 73 to 1251 within the nucleotide sequence shown in SEQ. ID No. 1 in the sequence listing,
(b) a DNA that hybridizes with a probe comprising a nucleotide sequence consisting of nucleotides 73 to 1251 within the nucleotide sequence shown in SEQ. ID No. 1 in the sequence listing or a part thereof under a stringent condition, and encodes a protein having a function of enhancing temperature tolerance.

(4) A microorganism whose temperature tolerance is enhanced by amplifying the intracellular copy number of the DNA described in the above-mentioned (2) or (3).

(5) The microorganism described in the above-mentioned (4) characterized in that the microorganism is an acetic acid bacterium belonging to the genus *Acetobacter* or the genus *Gluconacetobacter*.

(6) A method of producing vinegar characterized by culturing a microorganism having alcohol oxidation ability among the microorganisms described in the above-mentioned (4) or (5) in a medium containing alcohol, whereby acetic acid is produced and accumulated in the medium even at a high culture temperature.

(7) A recombinant plasmid pUCGCS (FERM BP-8217) including at least the DNA described in the above-mentioned (2) or (3).

(8) A recombinant plasmid pG1 or PGCS which is obtained by inserting PCR amplified fragments containing at least a DNA fragment having a nucleotide sequence shown in SEQ. ID No. 1 in the sequence listing (SalI-KpnI fragment) or a coding region thereof (nucleotides 73 to 1251), respectively, into, for instance, an acetic acid bacteria-*Escherichia coli* shuttle vector pGI18 (see, patent literature 2, for instance) not into an *Escherichia coli* vector pT7Blue as in (7).

(9) A transformant which is obtained by introducing a recombinant plasmid pG1 or PGCS into *Acetobacter aceti* No. 1023 (FERM BP-2287).

(10) A transformant which is obtained by introducing a recombinant plasmid pG1 or pGCS into *Acetobacter altoacetigenes* MH-24 (FERM BP-491).

According to the present invention, tolerance against temperature can be provided and enhanced for a microorganism. Moreover, in a microorganism having alcohol oxidation ability, particularly in acetic acid bacteria, tolerance against temperature can be remarkably improved and the ability of efficiently accumulating acetic acid even under a high temperature can be provided.

BEST MODE FOR CARRYING OUT THE INVENTION

Hereunder, the present invention will be described in detail.

(1) The DNA of the Present Invention

The DNA of the present invention comprises a nucleotide sequence that can encode a protein having a function of improving temperature tolerance and comprising an amino acid sequence shown in SEQ. ID No. 2 in the sequence listing, and it comprises an element for regulating the nucleotide sequence and a structural portion of the gene. In more detail, the present invention relates to a temperature-tolerance gene, and the temperature-tolerance gene means a gene participating in temperature tolerance and/or improvement of temperature tolerance. More specifically, the gene comprises at least one selected from at least (i) DNA having a nucleotide sequence shown in SEQ. ID No. 1 in the sequence listing and (ii) a nucleotide sequence of a gene that is included in (i) and encodes GCS protein (GCS gene).

The DNA of the present invention can be prepared by a method known to those skilled in the art. For example, DNA shown in a specific nucleotide sequence herein can be prepared by, for example, shotgun cloning with the use of a genome of acetic acid bacteria as a starting material. At this time, each of the fragmented chromosomal DNA is ligated to an appropriate cloning vector such as a plasmid vector or a phage vector depending on its size or the like, and an appropriate host cell such as an acetic acid bacterium is transformed with the use of this vector by an appropriate method such as electroporation, whereby a clone library for cloning each of the chromosomal DNA fragments can be prepared.

Further, determination of the nucleotide sequence of each of the chromosomal DNA fragments obtained from such a clone library can be carried out in accordance with a known method such as a chemical degradation method (Maxam-Gilbert method) or a dideoxy method.

Alternatively, the DNA of the present invention can be prepared by a chemical synthesis well-known to those skilled in the art or amplification by the PCR method with the use of a primer of the present invention based on the information of the nucleotide sequence of the DNA of the present invention or the amino acid sequence described herein.

For example, the DNA of the present invention can be obtained from chromosomal DNA of *Gluconacetobacter entanii* as follows. First, chromosomal DNA of *Gluconacetobacter entanii*, for example, *Acetobacter altoacetigenes* MH-24 strain (FERM BP-491) is obtained. Chromosomal DNA can be obtained by, for example, the method disclosed in Japanese Laid-Open Patent Application No. 60-9489.

Next, a chromosomal DNA library is prepared in order to isolate a gene for improving temperature tolerance from the obtained chromosomal DNA. To begin with, the chromosomal DNA is partially digested by a suitable restriction enzyme to obtain various chromosomal DNA fragment-mixtures. As the restriction enzyme, various kinds of restriction enzymes can be used, and the extent of cleavage is controlled by adjusting cleavage reaction time and the like depending on the used enzyme. For instance, chromosomal DNA is digested by the action of Sau3AI at a temperature of 30° C. or higher, preferably 37° C., at an enzyme concentration of 1 to 10 units/ml for various time periods (1 min to 2 h). Meanwhile, SalI and KpnI were used in the aftermentioned Examples.

Then, the digested fragments of chromosomal DNA are ligated to vector DNA that can replicate autonomously in acetic acid bacteria. Specifically, this vector DNA is completely digested by the action of a restriction enzyme which yields a terminal nucleotide sequence complementary to the restriction enzymes, SalI and KpnI, used in the digesting of the chromosomal DNA, for instance, SalI and KpnI, under the condition at a temperature of 37° C. and an enzyme concentration of 1 to 100 units/ml for 1 h or longer.

The digested vector DNA is mixed with the chromosomal DNA fragment-mixture, then a target recombinant DNA (DNA library) can be obtained by the action of $T_4$ DNA ligase. Incidentally, the condition for the action of $T_4$ DNA ligase can be set, for instance, at a temperature of 4 to 16° C. and an enzyme concentration of 1 to 100 units/ml for 1 h or longer, preferably 6 to 24 h.

Using the obtained recombinant DNA, an acetic acid bacterium, which can generally grow only at 37° C. on an agar medium, for instance *Acetobacter aceti* No. 1023 strain (FERM BP-2287) is transformed, and cultured at 38° C. A DNA fragment including a temperature-tolerance gene can be obtained by inoculating a formed colony into a liquid medium for cultivation, then recovering plasmids from the obtained bacterial cells.

As for the DNA of the present invention, DNA comprising a nucleotide sequence shown in SEQ. ID No. 1 in the sequence listing is specifically exemplified, among which the nucleotide sequence consisting of nucleotides 73 to 1251 within the nucleotide sequence is a coding region.

As a result of homology search on DDBJ/EMBL/Genbank and SWISS-PROT/PIR about the nucleotide sequence shown in SEQ. ID No. 1 and the amino acid sequence shown in SEQ. ID No. 2 (FIG. 4: corresponding to nucleotides 73 to 1251), it was found that they showed 41% homology with ceramide glucosyltransferase gene or *Mesorhizobium loti* and 39% homology with ceramide glucosyltransferase gene of Agrobacterium tumefaciens on an amino acid sequence level, but each of the homologies was low (around 40%), therefore, it was apparent that this was a novel gene and different from the genes encoding these proteins. In addition, it has been totally unknown that the above-mentioned ceramide glucosyltransferase gene participates in temperature tolerance.

As the nucleotide sequence of the DNA of the present invention was revealed, for instance, the DNA of the present invention can also be obtained by polymerase chain reaction (PCR reaction) with the use of the genomic DNA of acetic acid bacteria as a template and an oligonucleotide synthesized based on the nucleotide sequence as a primer, or by hybridization with the use of an oligonucleotide synthesized based on the nucleotide sequence as a probe, as well.

As for the synthesis of the oligonucleotide, it can be synthesized, for instance using commercially available various DNA synthesizers in the conventional manner. In addition, PCR reaction can be performed in the conventional manner using Thermal Cycler Gene Amp PCR System 9700 manufactured by Applied Biosystems and Taq DNA polymerase (manufactured by Takara Bio Inc.), KOD-Plus- (manufactured by TOYOBO Co., LTD.) and the like.

As for the DNA encoding a protein having a function of enhancing temperature tolerance of the present invention, it may be a DNA encoding a protein where one or several amino acids are deleted, substituted, inserted or added at one or several sites, as long as the function of enhancing temperature tolerance of the encoded protein is not impaired.

The DNA encoding a protein substantially identical to such a protein having a function of enhancing temperature tolerance can also be obtained by site directed mutation so that an amino acid at a specific site is deleted, substituted, inserted, added or inversed by site-directed mutagenesis, for instance. Further, the modified DNA as mentioned above can also be obtained by a conventionally known mutagenesis treatment.

In addition, since it is generally known that an amino acid sequence of a protein and a nucleotide sequence encoding the protein are slightly different among species, strains, mutants and variants, the DNA encoding a substantially identical protein can be obtained from general acetic acid bacteria, particularly from species, strains, mutants and variants of the genus *Acetobacter* or the genus *Gluconacetobacter*.

Specifically, DNA encoding a protein substantially identical to the protein can be obtained from acetic acid bacteria belonging to the genus *Acetobacter* or the genus *Gluconacetobacter*, acetic acid bacteria belonging to the genus *Acetobacter* or the genus *Gluconacetobacter* treated for mutagenesis, or natural mutants or variants thereof, by for instance, isolating DNA, which hybridizes under a stringent condition with DNA comprising a nucleotide sequence consisting of nucleotides 73 to 1251 within the nucleotide sequence shown in SEQ. ID No. 1 in the sequence listing and encodes a protein having a function of enhancing temperature tolerance.

The stringent condition here is a condition in which so-called a specific hybrid is formed while a non-specific hybrid is not formed. Though it is difficult to quantify this condition clearly, if one example is taken, a condition in which DNAs having high homology, for instance DNAs having homology of 70% or more hybridize, while DNAs having homology lower than this do not hybridize, or a condition in which general washing for hybridization is performed, for instance the washing is performed at a salt concentration equivalent to 1×SSC and 0.1% SDS at 60° C., can be exemplified.

The confirmation of having a function of enhancing temperature tolerance can be performed by, for instance, transforming *Acetobacter aceti* No. 1023 strain (FERM BP-2287), which can generally grow only at around 37° C. on an agar medium, with a target DNA, and investigating whether or not it can grow at 38° C. as explained in the after-mentioned Examples.

(2) The Acetic Acid Bacteria of the Present Invention

The acetic acid bacteria of the present invention mean bacteria belonging to the genus *Acetobacter* or the genus *Gluconacetobacter*, or such bacteria belonging to the genus *Acetobacter* or the genus *Gluconacetobacter* whose temperature tolerance is enhanced.

As for the bacteria belonging to the genus *Acetobacter*, *Acetobacter aceti* can be cited specifically, and for instance, *Acetobacter aceti* No. 1023 strain (deposited as FERM BP-2287 with International Patent Organism Depositary), *Acetobacter aceti* subsp. xylinum IFO 3288 strain and *Acetobacter aceti* IFO 3283 strain can be specifically exemplified.

Further, as for the bacteria belonging to the genus *Gluconacetobacter*, for instance, *Gluconacetobacter europaeus* DSM 6160 and *Gluconacetobacter entanii* can be cited, and for instance, *Acetobacter altoacetigenes* MH-24 strain (deposited as FERM BP-491 with International Patent Organism Depositary) can be specifically exemplified.

Temperature tolerance can be enhanced, for instance, by amplifying the intracellular copy number of a temperature-tolerance gene, or by transforming bacteria belonging to the genus *Acetobacter* with the use of recombinant DNA obtained by ligating a DNA fragment containing a structural gene of the gene to a promoter sequence that functions efficiently in the bacteria belonging to the genus *Acetobacter*.

In addition, temperature tolerance can also be enhanced by replacing the promoter sequence of the gene on chromosomal DNA with another promoter sequence functioning efficiently in bacteria belonging to the genus *Acetobacter* or the genus *Gluconacetobacter*, for instance a promoter sequence for alcohol dehydrogenase from acetic acid bacteria (see non-patent literature 8, for instance) or a promoter sequence derived from a microorganism other than acetic acid bacteria including a promoter for each gene such as an ampicillin-resistance gene for plasmid pBR322, a kanamycin-resistance gene for plasmid pACYC177, a chloramphenicol-resistance gene for plasmid pACYC184, a beta-galactosidase gene from *Escherichia coli*.

Amplification of the intracellular copy number of the gene can be conducted by introducing a multi-copy vector retaining the gene into cells of bacteria belonging to the genus *Acetobacter*, i.e. it can be conducted by introducing a plasmid, transposon or the like retaining the gene into cells of bacteria belonging to the genus *Acetobacter* or the genus *Gluconacetobacter*.

As for the multi-copy vector, a plasmid, transposon and the like can be exemplified. As for the plasmid, pMV24 (see non-patent literature 3, for instance), pGI18 (see non-patent literature 2, for instance), pUF106 (see non-patent literature 7, for instance), pTA5001 (A), pTA5001 (B) (see non-patent literature 1, for instance) and the like can be exemplified, and pMVL1 which is a chromosome-integrative type vector (see non-patent literature 4, for instance) can also be cited. Further, as for the transposon, Mu, IS1452 and the like can be exemplified.

Introduction of DNA into acetic acid bacteria belonging to the genus *Acetobacter* or the genus *Gluconacetobacter* can be performed by the calcium chloride method (see non-patent literature 5, for instance), the electroporation method (see non-patent literature 6, for instance) or the like.

Enhancement of temperature tolerance in acetic acid bacteria belonging to the genus *Acetobacter* or the genus *Gluconacetobacter* having alcohol oxidation ability in the above-described manner enables increase of the production efficiency of acetic acid.

(3) Method of Producing Vinegar

The method of producing vinegar of the present invention is characterized by culturing a microorganism which is a bacterium belonging to the genus *Acetobacter* or the genus *Gluconacetobacter* selectively enhanced its temperature tolerance by amplification of the copy number of a temperature-tolerance gene and which has alcohol oxidation ability in a medium containing alcohol, whereby acetic acid is produced and accumulated in the medium.

This method may be performed in the same manner as the conventional method of fermentation by acetic acid bacteria. The medium containing alcohol means a medium containing alcohol such as ethanol, carbon source, nitrogen source, inorganic substance and the like, and the one having a similar composition to that of a medium used in so-called acetic acid fermentation can be used. It may be either synthetic medium or natural medium as long as it contains a suitable amount of nutrition required by the used bacteria strain for its growth as needed. As for the carbon source, various kinds of carbohydrates such as glucose and sucrose and various kinds of organic acids can be used. As for the nitrogen source, natural nitrogen sources such as peptone, a degradation product of the fermentation bacteria and the like can be used.

In addition, the culture can be carried out in accordance with the usual methods such as static culture, shaking culture and aeration-agitation culture under aerobic condition. The culture temperature is 20 to 40° C., preferably 25 to 35° C. and can be generally set at 30° C. The pH of the medium is generally within the range of 2.5 to 7.0, preferably within the range of 2.7 to 6.5, and it can be adjusted with various kinds of acids, bases, buffers and the like as needed.

As mentioned above, in the present invention, by cultivation in a medium containing alcohol, acetic acid can be produced and accumulated in the medium. Generally, by cultivation of 1 to 21 days, acetic acid is produced and accumulated at higher concentration in the medium.

(4) Embodiment of the Present Invention

A recombinant plasmid PUCGCS which are made by inserting the ORF according to the present invention (nucleotides 73-1251 in SEQ. ID No. 1: GCS gene) or a part of the temperature-tolerance gene (SEQ. ID No. 1) containing the ORF into an *Escherichia coli* vector (multi-copy vector) pT7Blue (manufactured by Novagen Co.) has been deposited as FERM BP-8217 with International Patent Organism Depositary, so that the DNA of the gene according to the present invention can be obtained without difficulty, and a person skilled in the art would easily carry out the present invention. In addition, if it is desired, by using this recombinant plasmid, the ORF according to the present invention or a temperature-tolerance gene containing the ORF is transferred to a vector capable of replicating autonomously in acetic acid bacteria, and the vector is introduced into acetic acid bacteria and the acetic acid bacteria is cultured, whereby acetic acid fermentation can be carried out even under a high temperature condition and the cost for cooling can be reduced.

Further, as mentioned above and as it is also apparent from the after-mentioned Examples, the deposit of the source of the gene for enhancing temperature tolerance, the nucleotide sequence of the gene, the amino acid sequence of the protein corresponding to the gene, the embodiment of PCR, the preparation of a plasmid vector and a recombinant plasmid, the deposit of host bacteria and the like have been elucidated, and each of them can be obtained, operated and processed easily, therefore, if each operation and treatment is performed with reference to Examples, the target temperature-tolerant transformant can be obtained. The use of the transformant enables to produce acetic acid even under a high temperature condition.

Recombinant plasmid pUCGCS was deposited on Oct. 17, 2002 under the terms of the Budapest Treaty as FERM BP-8217 at the International Patent Organism Depositary National Instituted of Advanced Industrial Science and Technology, AIST Tsukuba Central 6, 1-1, Higashi 1-chome, Tuskuba-shi, Ibaraki-ken 305-8566, Japan.

Hereunder, the present invention will be explained more specifically with reference to Examples

EXAMPLES

Example 1

Cloning of Temperature-Tolerance Gene from *Gluconacetobacter entanii* and Determination of the Nucleotide Sequence and the Amino Acid Sequence (1) Generation of Chromosomal DNA Library

*Acetobacter altoacetigenes* MH-24 strain (FERM BP-491), which is one strain of *Gluconacetobacter entanii*, was cultured with shaking at 30° C. for 240 to 336 h in YPG medium (containing 3% glucose, 0.5% yeast extract and 0.2% polypeptone) to which 6% acetic acid and 4% ethanol were added. After the cultivation, the culture medium was centrifuged (7,500×g, 10 min) and bacterial cells were obtained. Chromosomal DNA was prepared from the obtained bacterial cells by the method disclosed in Japanese Laid-Open Patent Application No. 60-9489.

The obtained chromosomal DNA as mentioned above and the *Escherichia coli*-acetic acid bacteria shuttle vector pMV24 were digested with restriction enzymes SalI and KpnI (manufactured by Takara Bio Inc). These DNA in adequate amounts were mixed and ligated by using a ligation kit (TaKaRa DNA Ligation Kit Ver. 2, manufactured by Takara Bio Inc.), whereby a chromosomal DNA library of *Acetobacter altoacetigenes* MH-24 was constructed.

(2) Cloning of Temperature-Tolerance Gene

With the chromosomal DNA library of *Acetobacter altoacetigenes* MH-24 obtained in the above-described manner, *Acetobacter aceti* No. 1023 strain (FERM BP-2287) that generally can only grow at a growth temperature of up to around 37° C. on an agar medium was transformed. Subsequently, the transformed *Acetobacter aceti* No. 1023 strain was cultured for 4 days at 38° C. on YPG agar medium to which 100 µg/ml of ampicillin was added.

Then, the formed colony was inoculated into YPG medium containing 100 µg/ml of ampicillin and cultured, and plasmids were recovered from the obtained bacterial cells. As a result, a plasmid, in which a SalI-KpnI fragment of approximately 1.6 kbp as shown in FIG. 1 was cloned, could be recovered, and this plasmid was named pG1.

In this way, the DNA fragment for enhancing temperature tolerance, which enables *Acetobacter aceti* No.1023 strain that generally can only grow at up to around 37° C. on an agar medium to grow even at 38° C. was obtained.

(3) Determination of the Nucleotide Sequence of the Cloned DNA Fragment and the Amino Acid Sequence The cloned SalI-KpnI fragment described above was inserted into the SalI-KpnI cleavage site of pUC19, and the nucleotide sequence of the fragment was determined by Sanger's dideoxy chain termination method. Determination of the nucleotide sequence was conducted in all domains of the both strands of DNA, and it was also conducted in such a manner that the cleavage sites were overlapped.

As a result, the nucleotide sequence shown in SEQ. ID No. 1 in the sequence listing was determined. In nucleotides 73 to 1251 in the nucleotide sequence shown in SEQ. ID No. 1 in the sequence listing, the presence of the open reading frame (ORF) encoding the amino acid sequence consisting of 393 amino acids shown in SEQ. ID No. 2 in the sequence listing was confirmed.

Example 2

Enhancement of Temperature Tolerance in Transformant Transformed with Temperature-Tolerance Gene Derived from *Gluconacetobacter entanii*

(1) Transformation of *Acetobacter aceti*

The gene for enhancing temperature tolerance derived from *Acetobacter altoacetigenes* MH-24 strain (FERM BP-491) cloned as in Example 1 described above was amplified by the PCR method using KOD-Plus- (manufactured by TOYOBO Co., LTD). Then, PGCS was constructed by inserting the amplified fragment into the restriction enzyme SmaI cleavage site of the acetic acid bacteria-*Escherichia coli* shuttle vector pMV24 (see non-patent literature 3, for instance). The outline of the amplified fragment inserted into pGCS is shown in FIG. 1. This amplified fragment is included in the SalI-KpnI fragment (gene for improving temperature tolerance: the nucleotide sequence thereof is shown in SEQ. ID No. 1), and includes a part of the upstream and the downstream regions of the coding region (ORF) of the nucleotides 73 to 1251.

The PCR method was performed as follows; i.e. the PCR method was performed using genomic DNA derived from the above-mentioned acetic acid bacteria as a template and using primer 1 (the nucleotide sequence thereof is shown in SEQ. ID No. 3 (FIG. 5)) and primer 2 (the nucleotide sequence thereof is shown in SEQ. ID No. 4 (FIG. 6)) as a primer in the following condition.

(PCR Condition)

The PCR method was performed for 30 cycles with one cycle consisting of 94° C. for 15 sec, 60° C. for 30 sec and 68° C. for 2 min.

*Acetobacter aceti* No. 1023 strain (FERM BP-2287) was transformed with this pGCS by the electroporation method (see non-patent literature 6, for instance). The transformant was selected by culturing it on YPG agar medium, to which 100 μg/ml of ampicillin was added, at a culture temperature of 38° C.

It was confirmed that the transformant with ampicillin resistance grown on the selective medium retained the plasmid having the temperature-tolerance gene (GCS gene) by extracting the plasmid from the transformant in the conventional manner and analyzing it.

Example 3

Acetic Acid Fermentation Test of the Transformant Transformed with Temperature-Tolerance Gene Derived from *Gluconacetobacter entanii*

(1) Temperature Tolerance of the Transformant

The ampicillin-resistant transformant having the plasmid pGCS obtained in Example 2 was compared with the original strain of *Acetobacter aceti* No. 1023 into which only the shuttle vector pMV24 was introduced with regard to the growth in YPG medium when the culture temperature was changed.

Specifically, aeration-agitation culture was carried out in 1 L of YPG medium containing 1% acetic acid, 4% ethanol and 100 μg/ml of ampicillin using a 2-L mini-jar fermenter (Mitsuwa Rikagaku Kogyo Co.; KMJ-2A) at 400 rpm and 0.2 vvm, and the concentration of acetic acid in the culture medium and the growth for the transformant (by measuring the absorbance at 660 nm) was compared to those for the original strain. The culture temperature was 30° C. at first, then fermentation was performed at 33° C. until the concentration of acetic acid reached about 3%. Then, the temperature was further raised to 36° C. and fermentation was performed until the concentration of acetic acid reached 3%. Thereafter, the temperature was raised in 2° C. increments, and acetic acid fermentation was performed. When the concentration of acetic acid reached 3%, the culture medium was withdrawn except for about 100 ml of the culture medium, which was left in the mini-jar fermenter. To the remaining 100 ml of the culture medium, 900 ml of YPG medium was added in such a manner that the final concentrations of acetic acid, ethanol and ampicillin were 1%, 4% and 100 μg/ml, respectively, and the temperature was changed in the above-described manner, and acetic acid fermentation was restarted.

As a result, as shown in FIG. 2, while in the original strain of *Acetobacter aceti* No. 1023 strain, growth of bacteria and acetic acid fermentation could confirmed only up to 37° C., in the transformant, growth of bacteria and acetic acid fermentation were possible even at 38° C., and moreover, the result in which the growth was confirmed even at 40° C. was obtained, whereby the function of enhancing temperature tolerance of GCS gene was confirmed.

Example 4

Enhancement of Temperature Tolerance in the Transformant Transformed with Temperature-Tolerance Gene Derived from *Gluconacetobacter entanii*

(1) Transformation of *Acetobacter aceti*

The gene for enhancing temperature tolerance derived from *Acetobacter altoacetigenes* MH-24 strain (FERM BP-491) cloned as in Example 1 described above was amplified by the PCR method using KOD-Plus- (manufactured by TOYOBO Co., LTD.). Then, pGCS1 was constructed by inserting the acetic acid bacteria-*Escherichia coli* shuttle vector pGI18 (see non-patent literature 2, for instance) into the restriction enzyme SmaI cleavage site. The outline of the amplified fragment inserted into pGCS1 is shown in FIG. 1. This amplified fragment is included in the SalI-KpnI fragment (gene for improving temperature tolerance: the nucleotide sequence thereof is shown in SEQ. ID No. 1), and includes a part of the upstream and the downstream regions of the coding region (ORF) of the nucleotides 73 to 1251.

The PCR method was performed as follows; i.e. the PCR method was performed using the above-mentioned genomic DNA derived from acetic acid bacteria as a template and using primer 1 (the nucleotide sequence thereof is shown in SEQ. ID No. 3 (FIG. 5)) and primer 2 (the nucleotide sequence thereof is shown in SEQ. ID No. 4 (FIG. 6)) as a primer in the following condition.

(PCR Condition)

The PCR method was performed for 30 cycles with one cycle consisting of 94° C. for 15 sec, 60° C. for 30 sec and 68° C. for 2 min.

*Acetobacter aceti* No. 1023 strain (FERM BP-2287) was transformed with this pGCS1 by the electroporation method (see non-patent literature 6, for instance). The transformant was selected by culturing it on YPG agar medium, to which 100 μg/ml of ampicillin was added, at a culture temperature of 38° C.

It was confirmed that the transformant with ampicillin resistance grown on the selective medium retained the plasmid having the GCS gene by extracting the plasmid from the transformant in the conventional manner and analyzing it.

Figure 8:
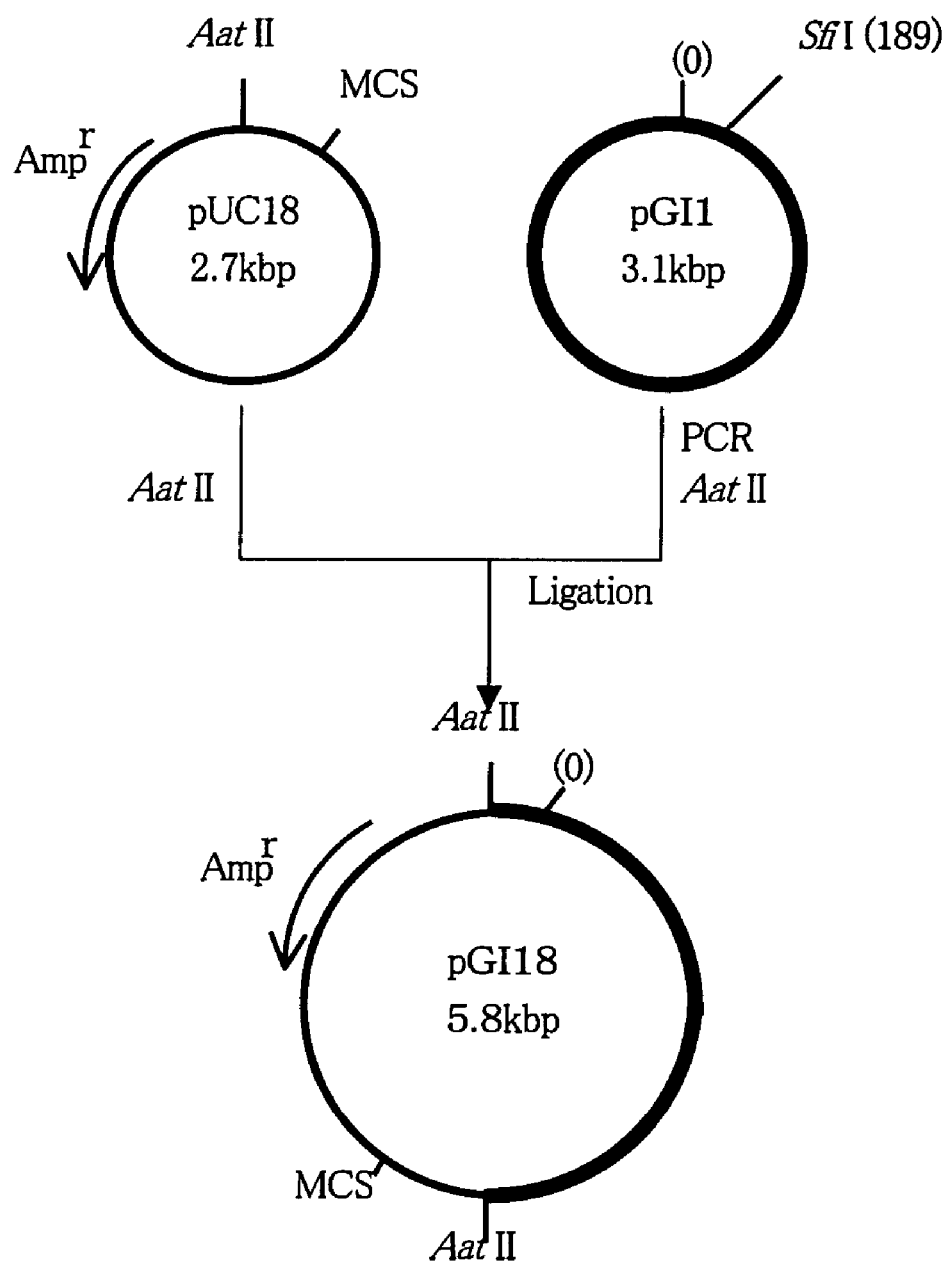
FIG. 8 This is a figure showing the construction of pGI18.

The vector pGI18 for acetic acid bacteria was constructed by the procedure shown in FIG. 8.

This vector pGI18 was constructed from the plasmids pGI1 and pUC18. First, the plasmid pGI1 was constructed. That is, *Acetobacter altoacetigenes* MH-24 strain (FERM BP-491), which is one strain of *Gluconacetobacter entanii*, was cultured with shaking at 30° C. for 240 h to 336 h in YPG medium (containing 3% glucose, 0.5% yeast extract and 0.2% polypeptone) to which 6% acetic acid and 4% ethanol were added. The obtained bacterial cells were lysated with sodium hydroxide or sodium dodecyl sulfate, then treated with phenol and further with ethanol, whereby the plasmid DNA was purified.

The obtained plasmid DNA was digested with various restriction enzymes (manufactured by Takara Bio Inc.) (at 37° C. and an enzyme concentration of 1 unit/ml), and the base-pair size of the obtained DNA fragments was determined by agarose electrophoresis.

The obtained plasmid DNA is a plasmid consisting of cyclic double stranded DNA having three HincII recognition sites and one SfiI recognition site, and the total size of the plasmid was about 3100 base pairs (bp). In addition, it had no recognition site for EcoRI, SacI, KpnI, SmaI, BamHI, XbaI, SalI, PstI, SphI and HindIII. The obtained plasmid DNA was named plasmid pGI1 and was used in construction of the vector pGI18 (FIG. 8).

The plasmid pGI1 obtained above was amplified by the PCR method using KOD-Plus- (manufactured by TOYOBO Co., LTD.) and digested with AatII.

The PCR method was performed as follows; i.e. the PCR method was performed using the plasmid pGI1 prepared in Example 1 as a template and using primer A and primer B having an AatII recognition site as a primer in the following condition. The nucleotide sequences of the primer A and the primer B are as shown in SEQ. ID No. 6 (FIG. 12) and in SEQ. ID No. 7 (FIG. 13), respectively.

The PCR condition was 30 cycles with one cycle consisting of 94° C. for 30 sec, 60° C. for 30 sec and 68° C. for 3 min.

On the other hand, pUC18 harboring an ampicillin (Amp)-resistance gene (manufactured by Takara Bio Inc.: 2686 bp) was digested with AatII (at 37° C. and an enzyme concentration of 1 unit/ml) and ligated to the plasmid pGI1 obtained above with $T_4$ DNA ligase. Then, Escherichia coli JM109 strain (manufactured by Takara Bio Inc.) was transformed in the conventional manner by using the reaction solution after ligation, and the transformant with Amp resistance was obtained by selection on a plate of LB medium (10 g of triptone, 5 g of yeast extract and 5 g of NaCl/L) containing 100 μg/ml of sodium ampicillin. From the obtained transformant, the plasmid was prepared, and the restriction enzyme cleavage pattern thereof was analyzed. In FIG. 8, the restriction enzyme map of the obtained plasmid is shown. In FIG. 8, "AatII" and "SfiI" indicate the restriction enzyme recognition sites. In addition, MCS indicates a multicloning site, $Amp^r$ indicates an ampicillin-resistance gene site, and a number in the parenthesis indicates the number of the nucleotide components represented by the bp unit. Further, "pUC18", "pGI1" and "pGI18" in the middle indicate the names of the plasmids, and "2.7 kbp", "3.1 kbp" and "5.8 kbp" indicate the total base numbers of the plasmids.

As is clear from FIG. 8, the obtained plasmid contained both pUC18 and pGI1, and the total size thereof was about 5800 base pairs (5.8 kbp). This plasmid was named vector pGI18 for acetic acid bacteria.

The nucleotide sequence of this vector pGI18 is shown in SEQ. ID No. 5 (FIG. 9, FIG. 10 and FIG. 11).

(2) Temperature Tolerance of the Transformant

The ampicillin-resistant transformant having the plasmid pGCS1 obtained in the above-described manner was compared with the original strain of Acetobacter aceti No. 1023 into which only the shuttle vector pGI18 was introduced with regard to the growth in YPG medium when the culture temperature was changed.

Specifically, aeration-agitation culture was carried out in 1 L of YPG medium containing 1% acetic acid, 4% ethanol and 100 μg/ml of ampicillin using a 2-L mini-jar fermenter (Mitsuwa Rikagaku Kogyo Co.; KMJ-2A) at 400 rpm and 0.2 vvm, and the concentration of acetic acid in the culture medium and the growth for the transformant (by measuring the absorbance at 660 nm) was compared to those for the original strain. The culture temperature was 30° C. at first, then fermentation was performed at 33° C. until the concentration of acetic acid reached about 3%. Then, the temperature was further raised to 36° C. and fermentation was performed until the concentration of acetic acid reached 3%. Thereafter, the temperature was raised in 2° C. increments, and acetic acid fermentation was performed. When the concentration of acetic acid reached 3%, the culture medium was withdrawn except for about 100 ml of the culture medium, which was left in the mini-jar fermenter. To the remaining 100 ml of the culture medium, 900 ml of YPG medium was added in such a manner that the final concentrations of acetic acid, ethanol and ampicillin were 1%, 4% and 100 μg/ml, respectively, and the temperature was changed in the above-described manner, and acetic acid fermentation was restarted.

As a result, as shown in FIG. 3, while in the original strain of Acetobacter aceti No. 1023 strain, growth of bacteria and acetic acid fermentation could confirmed only up to 37° C., in the transformant, growth of bacteria and acetic acid fermentation were possible even at 38° C., and moreover, the result in which the growth was confirmed even at 40° C. was obtained, whereby the function of enhancing temperature tolerance of GCS gene was confirmed.

Example 5

Acetic Acid Fermentation Test of the Transformant Transformed with Temperature-Tolerance Gene Derived from Gluconacetobacter entanii (1) Transformation of Acetobacter altoacetigenes Acetobacter altoacetigenes MH-24 strain (FERM BP-491), which is one strain of Gluconacetobacter entanii, was transformed with the plasmid pGCS1 obtained as in (Example 4) by the electroporation method (see non-patent literature 6, for instance). The transformant was selected with YPG agar medium containing 0.55% agar to which 100 μg/ml of ampicillin, 4% acetic acid and 4% ethanol were added.

It was confirmed that the transformant with ampicillin resistance grown on the selective medium retained the plasmid having the gene for enhancing temperature tolerance by extracting the plasmid from the transformant in the conventional manner and analyzing it.

(2) Acetic Acid Fermentation Test

The ampicillin-resistant transformant having the plasmid pGCS1 obtained in (1) was compared with the original strain of Acetobacter altoacetigenes MH-24 strain into which only the shuttle vector pGI18 was introduced with regard to the acetic acid fermentation ability.

Specifically, aeration-agitation culture was carried out in 2.5 L of a raw material medium (7% acetic acid, 3% ethanol, 0.2% yeast extract and 0.2% glucose) containing 100 μg/ml of ampicillin using a 5-L mini-jar fermenter (Mitsuwa Rikagaku Kogyo Co.; KMJ-5A) at 30° C., 500 rpm and 0.20 vvm. At the stage when apparent growth of bacteria was confirmed and the concentration of remaining ethanol reached 2%, a solution containing ethanol (1% acetic acid, 50% ethanol, 0.2% yeast extract and 0.2% glucose) was fed, whereby the concentration of ethanol in the fermentation liquid was maintained at 2%. By this method of performing acetic acid fermentation, acetic acid fermentation ability of the transformant was compared to that of the original strain. The result is summarized in Table 1.

TABLE 1

|  | Final acetic acid concentration (%) | Specific growth rate (OD 660/hr) | Production rate (%/hr) |
|---|---|---|---|
| Original strain | 15.6 | 0.0061 | 0.31 |
| Transformant | 17.2 | 0.0061 | 0.26 |

From the result of Table 1, it was confirmed that the transformant was remarkably superior in the final acetic acid concentration.

(3) Transformation of *Acetobacter aceti* subsp. xylinum

*Acetobacter aceti* subsp. xylinum IFO3288 strain, which is one strain of *Acetobacter aceti* subsp. xylinum, was transformed with the plasmid pGCS1 obtained as in (Example 4) by the electroporation method (see non-patent literature 6, for instance). The transformant was selected with YPG agar medium to which 100 μg/ml of ampicillin was added.

It was confirmed that the transformant with ampicillin resistance grown on the selective medium retained the plasmid having the gene for enhancing temperature tolerance by extracting the plasmid from the transformant in the conventional manner and analyzing it.

(4) Acetic Acid Fermentation Test

The ampicillin-resistant transformant having the plasmid pGCS1 obtained in (3) was compared with the original strain of *Acetobacter aceti* subsp. xylinum IFO3288 strain into which only the shuttle vector pGI18 was introduced with regard to the acetic acid fermentation ability.

Specifically, aeration-agitation culture was carried out using a raw material medium prepared by mixing 17.9% saccharified rice solution, 3.2% fermented moromi, 7.8% alcohol for brewing and 71.1% water at such a ratio (concentration of alcohol: 7.8%, concentration of acetic acid: 0.26%) in a 5-L mini-jar fermenter (Mitsuwa Rikagaku Kogyo Co.; KMJ-5A) at 30° C., 500 rpm and 0.20 vvm, and continuous fermentation at an acetic acid concentration of 7.2% was performed. The rates of adding the raw material medium in the continuous fermentation at an acetic acid concentration of 7.2% were compared, and the result is shown in Table 2. In addition, the acetic acid fermentation abilities were compared when the raw material medium addition rate for the transformant was conformed to the raw material medium addition rate for the original strain in the continuous fermentation at an acetic acid concentration of 7.2%. The result is shown in Table 3.

TABLE 2

|  | Acetic acid concentration (%) | OD 660 | Raw material medium addition rate (g/hr) |
|---|---|---|---|
| Original strain | 7.17 | 0.538 | 84.7 |
| Transformant | 7.26 | 0.612 | 96.3 |

TABLE 3

|  | Acetic acid concentration (%) | OD 660 | Raw material medium addition rate (g/hr) |
|---|---|---|---|
| Original strain | 7.24 | 0.502 | 82.3 |
| Transformant | 7.61 | 0.437 | 82.0 |

From the results of Table 2 and Table 3, it was confirmed that also in the continuous acetic acid fermentation, the transformant was remarkably superior in the productivity (raw material medium addition rate) and the concentration of produced acetic acid.

Industrial Applicability

According to the present invention, a novel gene participating in temperature tolerance can be provided, further a bred strain capable of highly efficient production vinegar under a higher temperature condition can be obtained by using the gene, and a method of highly efficient production vinegar under a higher temperature condition using the bred strain can be provided.

The invention claimed is:

1. An isolated polynucleotide which encodes a polypeptide comprising SEQ ID NO: 2 that enhances temperature tolerance of *Acetobacter* or *Gluconacetobacter*;
   wherein growth and/or acetic acid fermentation of an *Acetobacter* or *Gluconacetobacter* transformed with said polynucleotide is enhanced at a temperature above the optimal fermentation temperature for the corresponding untransformed strain.

2. The isolated polynucleotide of claim 1, which encodes a polypeptide consisting of SEQ ID NO: 2.

3. The isolated polynucleotide of claim 1, which comprises SEQ ID NO: 1.

4. A vector comprising the polynucleotide of claim 1.

5. An isolated host cell transformed with the vector of claim 4.

6. The host cell of claim 5, which is *Acetobacter* that exhibits enhanced growth and/or fermentation of acetic acid at a temperature above the optimal fermentation temperature for the corresponding untransformed strain.

7. The host cell of claim 5, which is *Gluconacetobacter* that exhibits enhanced growth and/or fermentation of acetic acid at a temperature above the optimal fermentation temperature for the corresponding untransformed strain.

8. A method for producing acetic acid comprising culturing the host cell of claim 5, which is *Acetobacter* or *Gluconacetobacter* that exhibits enhanced growth and/or fermentation of acetic acid at a temperature above the optimal fermentation temperature for the corresponding untransformed strain.

9. An isolated polypeptide encoded by the polynucleotide of claim 1.

10. The isolated polypeptide of claim 9, which consists of SEQ ID NO: 2.

11. The isolated polynucleotide consisting of nucleotides 73 to 1251 of SEQ ID NO: 1.

12. The recombinant plasmid pUCGCS deposited as FERM BP-8217.

13. An isolated polynucleotide which encodes a polypeptide comprising SEQ ID NO: 2 or a fragment of SEQ ID NO: 2 that enhances temperature tolerance when expressed in *Acetobacter* or *Gluconacetobacter*;
   wherein growth and/or acetic acid fermentation of an *Acetobacter* or *Gluconacetobacter* transformed with said polynucleotide is enhanced at a temperature above the optimal fermentation temperature for the corresponding untransformed strain.

14. A vector comprising the polynucleotide of claim 13.

15. An isolated host cell transformed with the vector of claim 14.

16. A method for producing acetic acid comprising culturing the host cell of claim 15, which is *Acetobacter* or *Gluconacetobacter* that exhibits enhanced growth and/or fermentation of acetic acid at a temperature above the optimal fermentation temperature for the corresponding untransformed strain.

17. An isolated polypeptide encoded by the polynucleotide of claim 13.

* * * * *

SEQUENCE LISTING

<160> NUMBER OF SEQ ID NOS: 7

<210> SEQ ID NO 1
<211> LENGTH: 1313
<212> TYPE: DNA
<213> ORGANISM: Gluconacetobacter entanii

<400> SEQUENCE: 1

```
gaagagtgat attacacttc cctgacgccg ttttctaatt tgctccatac gcgggacctt      60
gccggaaaga taatgtctgt tttcaacgct cttgtttcac ccgccggact ggccgcgacc     120
gttgcggtcg ccgggtgcat gcaggcagcg cttggcactt ttctggtctc gcgtttccgg     180
tggcaggaaa aacgcatgga ccgggcggtg cccatgcctc cggtttccgt gctcaagccc     240
ctccacggcg atgaaccgct gctggaggaa gcgcttgaaa gcttctgcac gcaggattac     300
```

-continued

| | |
|---|---|
| ccgcagatgc agatcgtctt tggcgtacag gccgaagacg atgcggcgat cccgatcgta | 360 |
| caacggttga tggaacgcca cccggatgtg cagatggaac tggtgattga ccccaccttc | 420 |
| cacgggctca accgcaagat cggcaacctg atcaacatca tgacgcgcgt gaagcatgat | 480 |
| gtcctggtca tttccgattc ggatatccac gttgccccg attacctgcg gcatgtggtg | 540 |
| ggcgccatgg tgcccgacaa tgtcggcctg tcacgacgc tgtacgcggg gctgcccgcg | 600 |
| tcatccacgc tgccgcgcct gctggccgca tgccagatca accataactt cctgcccggc | 660 |
| gtgatgctgt cactctacct cgggcggcag gactgccttg gggcgacaat ggcgctgcgg | 720 |
| cgttccatgc tggacgaaat cggcgggctg aagccctcg tgccgcatgt ggccgatgat | 780 |
| gcgatactgg ccgttacgt gcgtgaccgt ggcaaggata tcgccattgc cgcgtgcatg | 840 |
| acctggacca ccgtgggcga gacctcgatg cgtgaggtgc tggcgcatga actgcgctgg | 900 |
| ggccggaccg tcaagacgct ggagcctgcg ggttatgccg catccgccat ccagctgccc | 960 |
| ctgttctggg ccagcgtcgc cgtgcttgcc gcgccgcatg cgacctggac atggtccttc | 1020 |
| tttcttggtg catggggatg gcgggccgtg tgttccttca tcctggaccg tacgctggcg | 1080 |
| caacgtagtc tggtgctgcc gtcactgctt ctgccactgc gcgactggat ctcggccgcc | 1140 |
| gtcatggtgg gcagtgtcac tggcacgcgg gttgcatggc gtgggcagac aatgcatgtc | 1200 |
| acgccccatt cggtcatgac accacgatcg caaccggctt cccccggtga ctgacccgcc | 1260 |
| gtcagcaggc tgaactgctt gagaattcca accctgtcgt taataagaac ggg | 1313 |

<210> SEQ ID NO 2
<211> LENGTH: 393
<212> TYPE: PRT
<213> ORGANISM: Gluconacetobacter entanii

<400> SEQUENCE: 2

Met Ser Val Phe Asn Ala Leu Val Ser Pro Ala Gly Leu Ala Ala Thr
              5                   10                  15

Val Ala Val Ala Gly Cys Met Gln Ala Ala Leu Gly Thr Phe Leu Val
          20                  25                  30

Ser Arg Phe Arg Trp Gln Glu Lys Arg Met Asp Arg Ala Val Pro Met
      35                  40                  45

Pro Pro Val Ser Val Leu Lys Pro Leu His Gly Asp Glu Pro Leu Leu
  50                  55                  60

Glu Glu Ala Leu Glu Ser Phe Cys Thr Gln Asp Tyr Pro Gln Met Gln
65                  70                  75                  80

Ile Val Phe Gly Val Gln Ala Glu Asp Ala Ala Ile Pro Ile Val
              85                  90                  95

Gln Arg Leu Met Glu Arg His Pro Asp Val Gln Met Glu Leu Val Ile
          100                 105                 110

Asp Pro Thr Phe His Gly Leu Asn Arg Lys Ile Gly Asn Leu Ile Asn
      115                 120                 125

Ile Met Thr Arg Val Lys His Asp Val Leu Val Ile Ser Asp Ser Asp
  130                 135                 140

Ile His Val Ala Pro Asp Tyr Leu Arg His Val Val Gly Ala Met Val
145                 150                 155                 160

Pro Asp Asn Val Gly Leu Val Thr Thr Leu Tyr Ala Gly Leu Pro Ala
              165                 170                 175

Ser Ser Thr Leu Pro Arg Leu Leu Ala Ala Cys Gln Ile Asn His Asn
          180                 185                 190

Phe Leu Pro Gly Val Met Leu Ser Leu Tyr Leu Gly Arg Gln Asp Cys

-continued

```
                   195                 200                 205
Leu Gly Ala Thr Met Ala Leu Arg Arg Ser Met Leu Asp Glu Ile Gly
    210                 215                 220
Gly Leu Glu Ala Leu Val Pro His Val Ala Asp Ala Ile Leu Gly
225                 230                 235                 240
Arg Tyr Val Arg Asp Arg Gly Lys Asp Ile Ala Ile Ala Ala Cys Met
                245                 250                 255
Thr Trp Thr Thr Val Gly Glu Thr Ser Met Arg Glu Val Leu Ala His
                260                 265                 270
Glu Leu Arg Trp Gly Arg Thr Val Lys Thr Leu Glu Pro Ala Gly Tyr
            275                 280                 285
Ala Ala Ser Ala Ile Gln Leu Pro Leu Phe Trp Ala Ser Val Ala Val
    290                 295                 300
Leu Ala Ala Pro His Ala Thr Trp Thr Trp Ser Phe Phe Leu Gly Ala
305                 310                 315                 320
Trp Gly Trp Arg Ala Val Cys Ser Phe Ile Leu Asp Arg Thr Leu Ala
                325                 330                 335
Gln Arg Ser Leu Val Leu Pro Ser Leu Leu Leu Pro Leu Arg Asp Trp
            340                 345                 350
Ile Ser Ala Ala Val Met Val Gly Ser Val Thr Gly Thr Arg Val Ala
            355                 360                 365
Trp Arg Gly Gln Thr Met His Val Thr Pro His Ser Val Met Thr Pro
    370                 375                 380
Arg Ser Gln Pro Ala Ser Pro Gly Asp
385                 390         393

<210> SEQ ID NO 3
<211> LENGTH: 30
<212> TYPE: DNA
<213> ORGANISM: Artificial Sequence
<220> FEATURE:
<223> OTHER INFORMATION: Primer 1

<400> SEQUENCE: 3
gaagagtgat attacacttc cctgacgccg                                        30

<210> SEQ ID NO 4
<211> LENGTH: 26
<212> TYPE: DNA
<213> ORGANISM: Artificial Sequence
<220> FEATURE:
<223> OTHER INFORMATION: Primer 2

<400> SEQUENCE: 4
cccgttctta ttaacgacag ggttgg                                            26

<210> SEQ ID NO 5
<211> LENGTH: 5734
<212> TYPE: DNA
<213> ORGANISM: Gluconacetobacter entanii (Acetobacter altoacetigenes
      MH-24)

<400> SEQUENCE: 5
catggggcgt caccccccagc ggccagcttg gctacctgat ggacagggcg ggccttctgc      60
aagccctcgg ccactgccat ctgccgggat atgaggccaa atacgaaccg aaggaaaagc     120
gcaccttctg ctaccccacc cagaacgcca gcggctgggc tgtgcagcca tgatcgccaa     180
cccctccctc ttcctgagca attcggaaga gcgatttccg ccgactgaac acgtcgaaaa     240
```

-continued

```
tggcagtttt ccaccgaaaa aaggaaagga ccataggaaa ggattaatat cttatttta      300 tctaggggtt tgccgatccg cgattttcgc tgggaaaccg ccaaaaatgg cttgccatta      360
ggtcgcacca catgcgacca taaagtcgca cagtgtgcga cctattcggc ccatatacag      420
aggttcccca catgcggaat gtcacccgtc tcaagacccg caaagaccgg ctccgcgagg      480
accaagccga cctgttgaag caagcccttc tgcccttcgc agaggacgat ggaccgatgc      540
gggatgcggt cggacggctc tacgtccaga tcaagaacct caccaccccca gaccccggaa      600 ccacggagcc gttcgtcatg atccgtcccg cccagaatcg cgccgtcacc ctctggctgc      660
tgaagaacag taagcggccc atgaaggccg tggacgtatg gacgctgctg ttcgaccacc      720
tgtttcccca taccggccag atcatgctga cccgtgagga atcgcggaa aaagtcggta       780 tccgggtcaa cgaagttaca gccgtcatga acgagctggt gagcttcggc gcgattttct      840
ccgagcgcga gaaggtggcc ggaatgcgcg ggccgggcct cgcccgctac tacatgaacc      900
ggcatgtggc cgaggtcggc agccgcgcca cgcaggaaga acttgcccta atcccacgcc      960
ccggcgccaa gctggcagtc gtgcagggtg gcaaggctta acccatgaag gtttcggaac     1020
tggacgtgtt cgacacgcgcc aaggcggcac aagacccgtt ggtgcgggaa gaactgctgc    1080
aagcagcgca ggcggacggc cacggccccg ccctcgctca tgcccgttcc gtcatagcca     1140
aggcgcgggc cggcgcaggac gccaaggctt aacggccccg ccctctcccg cctcgatccc    1200
ggcgggcctg tagcatctcc tgatgctcct tggcgttttt ggcccgctgc tcggcccgct     1260 cttctcggc cgctgcggct cttaggcgct cttcggccag ccgcatccgc tcgtccatct      1320
gacgtttccg atctgcctcg gcatccttgg cggctcctgc cttcagccct ttgctgaaag     1380
ccatccactt attggcggtt ttctcggctt tctgctgtat cggcggggtc agccggtcaa     1440
atgcctgggc caccctctcg aagccctcac gcatggcgtt gacggcctgc gccagtttag     1500
ccagggcgaa atctatcacc tcggcccgct gggcgttctc ggcccggata cgccggttgt     1560
ggttgccggt cggggtctgg tggccctcc gttccagagc caccacattc ggccccatgt      1620
gccgctctgg aacgcggtct agcccctgct ccgcattgct ccggtgatct atccgggcct    1680
cttgcccagc ccgctctagc gcggcattgg caaggcccgc ccatagctgc cggatttcct     1740
tcacctcgtc ggcggccttc cccagtccca tgccctgccg cttcttgtcg gacagttcga     1800
tggttgattt gtctccaaag gacagcttgc catcggcccc ccgctccacc gtgcgggtgg     1860
tggtcatgat gtgcgcgtga tgattccggt cgtcgccctc gtcacccgga agatgcacgg     1920
ccacgtccac ggccacccg taccgctgga ccaactcacg cgcgaaactg tccgccagtt      1980
cggcccgctg ctcgctggtg agttcatgag ggagggccac aacccattcc ctccgggtgc     2040
gggcgtcctt gcgtttctct gatcgctccg cgtcattcca caattccgaa cggtcagcgg    2100
tgccaccccc cggaatgaaa attgccttat gggcaacgct attctgcctg gggctgtatt     2160
tgtgttcgtg cccgtcaacc tcgttggtca atcctcgcc agcacgatac gcagccgcag      2220
ccacaacgga acgccctgcg ctccggctga tcggtttcgt ttctgcgcga tagattgcca     2280
cggatcgagc gcctacctt tggagttaaa cggggggttc agggggggcga agccaccatg     2340 acgcaggact tgcacttgtg caagtcgtaa ctgcgccctt aatacctgac ggcatcaagg     2400
gatatgtggt attcgtttga aacggaacgg ctccacggtg aggatgatat gagcgatatt     2460
gcgaaagaga ttgagaacgc caaaaggatc atagctgaac agaaaaagcg catcaaagat     2520
gcccagaagg aagcagctaa agcggaatca aagttgaggg accgtcagaa ctacatcttg     2580
ggcggcgcac tggtaaaact tgccgaaaca gatgaacggg ccgtccgcac tattgaaaca     2640
```

```
cttttgaagc tggtggatcg tccatcagac cggaaggcgt ttgaggtgtt ttcccgtctc   2700
ccatccctct ccctgcccac gcagccagca ccggacaccg gccatgagtg aggcactgga   2760
agaagatccg tttgaactgt tcaaaagggt cgaaaaaagc ctgtccacgg ccaccgccag   2820
catggagcgg ctggccgccg aacaagatgc caggtgcaag accatttcag acgccgccgg   2880
aaaagcctct aaattggccg aggaagccgg tgacaccttc acagcatcca agaggcgtct   2940
gatgatctgg acggccctct cgcgggctct gctggtctgt ggcgggtggt tggcgggtta   3000
ttggctggga caccgtgacg gttgggcctc tggcacggcc cacgacgtct aagaaaccat   3060
tattatcatg acattaacct ataaaaatag gcgtatcacg aggccctttc gtctcgcgcg   3120
tttcggtgat gacggtgaaa acctctgaca catgcagctc ccggagacgg tcacagcttg   3180
tctgtaagcg gatgccggga gcagacaagc ccgtcagggc gcgtcagcgg gtgttggcgg   3240 gtgtcgggc tggcttaact atgcggcatc agagcagatt gtactgagag tgcaccatat   3300
gcggtgtgaa ataccgcaca gatgcgtaag gagaaaatac cgcatcaggc gccattcgcc   3360
attcaggctg cgcaactgtt gggaagggcg atcggtgcgg gcctcttcgc tattacgcca   3420
gctggcgaaa gggggatgtg ctgcaaggcg attaagttgg gtaacgccag ggttttccca   3480
gtcacgacgt tgtaaaacga cggccagtgc caagcttgca tgcctgcagg tcgactctag   3540
aggatccccg ggtaccgagc tcgaattcgt aatcatggtc atagctgttt cctgtgtgaa   3600
attgttatcc gctcacaatt ccacacaaca tacgagccgg aagcataaag tgtaaagcct   3660
ggggtgccta atgagtgagc taactcacat taattgcgtt gcgctcactg cccgctttcc   3720
agtcgggaaa cctgtcgtgc cagctgcatt aatgaatcgg ccaacgcgcg gggagaggcg   3780
gtttgcgtat tgggcgctct tccgcttcct cgctcactga ctcgctgcgc tcggtcgttc   3840
ggctgcggcg agcggtatca gctcactcaa aggcggtaat acggttatcc acagaatcag   3900
gggataacgc aggaaagaac atgtgagcaa aaggccagca aaaggccagg aaccgtaaaa   3960
aggccgcgtt gctggcgttt ttccataggc tccgcccccc tgacgagcat cacaaaaatc   4020
gacgctcaag tcagaggtgg cgaaacccga caggactata aagataccag gcgtttcccc   4080
ctggaagctc cctcgtgcgc tctcctgttc cgaccctgcc gcttaccgga tacctgtccg   4140
cctttctccc ttcgggaagc gtggcgcttt ctcaatgctc acgctgtagg tatctcagtt   4200
cggtgtaggt cgttcgctcc aagctgggct gtgtgcacga accccccgtt cagcccgacc   4260
gctgcgcctt atccggtaac tatcgtcttg agtccaaccc ggtaagacac gacttatcgc   4320
cactggcagc agccactggt aacaggatta gcagagcgag gtatgtaggc ggtgctacag   4380
agttcttgaa gtggtggcct aactacggct acactagaag gacagtattt ggtatctgcg   4440
ctctgctgaa gccagttacc ttcggaaaaa gagttggtag ctcttgatcc ggcaaacaaa   4500
ccaccgctgg tagcggtggt ttttttgttt gcaagcagca gattacgcgc agaaaaaaag   4560
gatctcaaga agatcctttg atcttttcta cggggtctga cgctcagtgg aacgaaaact   4620
cacgttaagg gattttggtc atgagattat caaaaaggat cttcacctag atccttttaa   4680
attaaaaatg aagttttaaa tcaatctaaa gtatatatga gtaaacttgg tctgacagtt   4740
accaatgctt aatcagtgag gcacctatct cagcgatctg tctatttcgt tcatccatag   4800
ttgcctgact ccccgtcgtg tagataacta cgatacggga gggcttacca tctggcccca   4860
gtgctgcaat gataccgcga gacccacgct caccggctcc agatttatca gcaataaacc   4920
agccagccga aagggccgag cgcagaagtg gtcctgcaac tttatccgcc tccatccagt   4980
```

-continued

```
ctattaattg ttgccgggaa gctagagtaa gtagttcgcc agttaatagt ttgcgcaacg    5040
ttgttgccat tgctacaggc atcgtggtgt cacgctcgtc gtttggtatg gcttcattca    5100
gctccggttc ccaacgatca aggcgagtta catgatcccc catgttgtgc aaaaaagcgg    5160
ttagctcctt cggtcctccg atcgttgtca gaagtaagtt ggccgcagtg ttatcactca    5220
tggttatggc agcactgcat aattctctta ctgtcatgcc atccgtaaga tgcttttctg    5280
tgactggtga gtactcaacc aagtcattct gagaatagtg tatgcggcga ccgagttgct    5340
cttgcccggc gtcaatacgg gataataccg cgccacatag cagaacttta aaagtgctca    5400
tcattggaaa acgttcttcg gggcgaaaac tctcaaggat cttaccgctg ttgagatcca    5460
ttcgatgtaa cccactcgtg cacccaactg atcttcagca tcttttactt tcaccagcgt    5520
ttctgggtga gcaaaaacag gaaggcaaaa tgccgcaaaa aagggaataa gggcgacacg    5580
gaaatgttga atactcatac tcttcctttt tcaatattat tgaagcattt atcagggtta    5640
ttgtctcatg agcggataca tatttgaatg tatttagaaa aataaacaaa tagggttcc     5700 gcgcacattt ccccgaaaag tgccacctga cgtc                                5734
```

<210> SEQ ID NO 6
<211> LENGTH: 30
<212> TYPE: DNA
<213> ORGANISM: Artificial sequence
<220> FEATURE:
<223> OTHER INFORMATION: Primer A

<400> SEQUENCE: 6
cgctgacgtc gtgggccgtg ccagaggccc    30

<210> SEQ ID NO 7
<211> LENGTH: 30
<212> TYPE: DNA
<213> ORGANISM: Artificial sequence
<220> FEATURE:
<223> OTHER INFORMATION: Primer B

<400> SEQUENCE: 7
ggccaagacg tctgcagcat ggggcgtcac    30